US008820581B2

(12) United States Patent
Baldelli

(10) Patent No.: US 8,820,581 B2
(45) Date of Patent: Sep. 2, 2014

(54) DISPENSING DEVICE FOR MULTI-COMPONENT CARTRIDGES

(71) Applicant: Sulzer Mixpac AG, Haag (CH)

(72) Inventor: Enrico Baldelli, Altdorf (CH)

(73) Assignee: Sulzer Mixpac AG, Haag (CH)

( * ) Notice: Subject to any disclaimer, the term of this patent is extended or adjusted under 35 U.S.C. 154(b) by 0 days.

(21) Appl. No.: 13/713,911

(22) Filed: Dec. 13, 2012

(65) Prior Publication Data

US 2013/0161353 A1    Jun. 27, 2013

(30) Foreign Application Priority Data

Dec. 22, 2011  (EP) .................................... 11195135

(51) Int. Cl.
| | | |
|---|---|---|
| *B67D 7/70* | (2010.01) | |
| *B65D 83/00* | (2006.01) | |
| *A61C 9/00* | (2006.01) | |
| *B05C 17/005* | (2006.01) | |
| *B05C 17/01* | (2006.01) | |

(52) U.S. Cl.
CPC .......... *B65D 83/0033* (2013.01); *A61C 9/0026* (2013.01); *B05C 17/00553* (2013.01); *B05C 17/0126* (2013.01); *B05C 17/00596* (2013.01)
USPC ........................................ 222/137; 222/145.5

(58) Field of Classification Search
CPC  B05C 17/0123; B05C 17/01; B05C 17/0109; B56D 83/0033
USPC ......... 222/137, 136, 391, 145.1, 145.5, 145.6
See application file for complete search history.

(56) References Cited

U.S. PATENT DOCUMENTS

| | | | | |
|---|---|---|---|---|
| 3,767,085 A | * | 10/1973 | Cannon et al. ................... | 222/82 |
| 5,005,735 A | * | 4/1991 | Keller ........................... | 222/137 |
| 5,336,014 A | * | 8/1994 | Keller ............................. | 403/24 |
| 5,743,436 A | * | 4/1998 | Wilcox et al. .................. | 222/137 |
| 5,875,928 A | * | 3/1999 | Muller et al. ................... | 222/82 |

(Continued)

FOREIGN PATENT DOCUMENTS

| | | |
|---|---|---|
| CH | 703 427 A1 | 1/2012 |
| EP | 0 543 776 A1 | 5/1993 |

(Continued)

OTHER PUBLICATIONS

European search report for corresponding EP 11195135.6.-2425 issued on Jun. 8, 2012.

*Primary Examiner* — Lien Ngo
(74) *Attorney, Agent, or Firm* — K&L Gates LLP

(57) ABSTRACT

A dispensing device for a multi component cartridge includes a housing in which a reception element for receiving a cartridge end of the multicomponent cartridge is arranged. The cartridge end is located at the inlet side of a first and second storage container filled with a filling mass and respectively sealed in a fluid tight manner at the cartridge end by a respective piston. A plunger arrangement and a drive arrangement for moving the plunger arrangement are arranged in the housing. A movement of the plunger arrangement in a dispensing direction can be carried out by the drive arrangement for dispensing the filling mass from the storage containers of the multicomponent cartridge. The reception element has an axis of rotation which is substantially arranged in parallel to the dispensing direction. The cartridge end pushed into the reception element can be transferred from an assembly position into a dispensing position by a rotation about the axis of rotation.

14 Claims, 4 Drawing Sheets

(56) References Cited

U.S. PATENT DOCUMENTS

| | | |
|---|---|---|
| 5,924,600 A | 7/1999 | Keller |
| 5,992,694 A | 11/1999 | Keller |
| 6,047,864 A | 4/2000 | Winkler |
| 6,182,867 B1 | 2/2001 | Keller |
| 8,141,753 B2 * | 3/2012 | Ostermeier et al. .......... 222/326 |
| 8,286,832 B2 | 10/2012 | Keller |
| 2008/0314929 A1 | 12/2008 | Keller |

FOREIGN PATENT DOCUMENTS

| | | |
|---|---|---|
| EP | 0 791 403 A1 | 8/1997 |
| EP | 0 791 404 A1 | 8/1997 |
| EP | 0 885 599 A2 | 12/1998 |
| WO | 2007/073607 A1 | 7/2007 |
| WO | 2012006749 A1 | 1/2012 |

* cited by examiner

DISPENSING DEVICE FOR MULTI-COMPONENT CARTRIDGES

PRIORITY CLAIM

The present application claims priority to European Patent Application No. 11195135.6 filed on Dec. 22, 2011, the disclosure of which is incorporated herein by reference.

BACKGROUND

The present application relates to a dispensing device for multi-component cartridges which are manually actuatable.

Such dispensing devices are, for example, known from EP 0 791 403 B1 or from EP 0 791 404 B1. The two-component cartridge described in EP 0 791 403 B1 has two storage containers which are formed there as cylinders having the same cross-sectional area. The inlet side cartridge end is formed as a flange connecting the two cylinders. A coding means is attached in the flange in order to correctly position the cylinders in the dispensing device. The dispensing device has a recess matching the flange in which the flange is stuck from above. In particular, when the filling mass is viscous and slow moving large dispensing forces act on the dispensing device on the upper open end of the mount for the flange of the dispensing end of the two-component cartridge.

For this reason a safety cap is provided in EP 0 791 404 B1 or in EP 0 543 776 B1 which presses the flange from above towards the housing of the dispensing apparatus. However, this measure has been found not be sufficient for viscous slow moving filling masses, since the safety cap can be damaged and can even be broken due to the large forces. In particular, for mixing ratios deviating from a 1:1 mixing ratio it is true that the multi-component cartridge can be unevenly loaded via the longitudinal side of the flange. This can lead to the formation of a tilting torque so that also in this case an uneven load distribution can result in the safety cap which leads to damage at a safety cap.

The post-published CH 703 427 A1 describes a dispenser for discharging at least one flowable component from a cartridge. The dispenser has a cartridge holder and an advancing element that can be moved in said holder along an advancing direction. A cartridge can be inserted axially into the cartridge holder against the advancing direction. A rotating element is attached to the cartridge holder in order to axially fix the cartridge. The cartridge can be inserted into the cartridge holder against the advancing direction in a first orientation, while the rotating element axially fixes the inserted cartridge in the second orientation. There is no rotation of the cartridge during the rotation of the rotating element from the first to the second orientation and so during the axial fixing of the cartridge.

SUMMARY

It is an object of the present application to provide an alternative attachment of the flange of the cartridge end in the dispensing device which dispensing device has a longer operating life because the mount for the flange of the cartridge end is subjected to lesser forces by means of an improved load distribution.

It is a further object of the present application to provide a dispensing device enabling a simplified handling and exchange of the multi-component cartridge.

The object of the present application is satisfied by a dispensing device which has the following features: the dispensing device for a multi-component cartridge includes a housing in which a reception element for receiving a cartridge end of the multi-component cartridge is arranged. The cartridge end is located at the inlet side of the multi-component cartridge. The multi-component cartridge in the shape of a two-component cartridge has a first and second storage container each filled with a filling mass and which are each sealed in a fluid-tight manner at the cartridge end by a respective piston. A plunger arrangement and a drive arrangement for moving the plunger arrangement are arranged in the housing. A movement of the plunger arrangement in a dispensing direction can be carried out by the drive arrangement for dispensing the filling mass from the storage containers of the multi-component cartridge. The reception element has an axis of rotation which is substantially arranged in parallel to the dispensing direction. The cartridge end pushed into the reception element can be transferred from an assembly position into a dispensing rotation by means of a rotation about the axis of rotation. The multi-component cartridge is particularly installed into the reception element crossways to the dispensing direction.

The angle of rotation for the rotation of the cartridge end from the assembly position into the dispensing position advantageously amounts to substantially 90°. Hereby it is ensured that the load distribution is as uniform as possible and that the cartridge end is, in particular completely received in the reception element apart from a narrow insertion section.

In accordance with an embodiment the reception element is rotatably arranged in a guide element. For this purpose the guide element can be inseparably connected to the housing in the installed state. In particular, the reception element can be rotatably supported in the guide element in the housing. The guide element can be formed as a projection and can be received in a groove of the reception element.

On assembly of the cartridge end and the reception element, the first and second storage containers are displaceable between a second opening for the second storage container and a first opening for the first storage container along the connection line extending between the longitudinal axes of the first and second storage containers. Hereby it is ensured that insertion takes place via the smallest dimension, the width dimension of the flange of the cartridge end.

In accordance with an embodiment, the reception element has a guide groove for receiving the cartridge end. In particular, the reception element or the guide element can have an abutment in order to limit the rotation between the assembly position and the dispensing position. The reception element can have an abutment and/or a latch element for securing the multi-component cartridge in the dispensing position and/or in the assembly position, in particular the reception element has a latch element for latching in the dispensing position and/or in the assembly position. A clicking sound can be emitted on latching, so that the latching is audible for the user.

In accordance with each of the embodiments, the cartridge end can be inserted into the reception elements and can be removed again from the reception element. The reception element can have a coding element for the correct positioning of the storage containers of the multi-component cartridge. In particular, the coding elements can include a first opening and a second opening in which a respective storage container of the multi-component cartridge can be received, with the diameter of the first opening being different from the diameter of the second opening.

The drive arrangement can, for example, effect a movement of the plunger arrangement in the direction of the dispensing end of a multi-component cartridge by means of an actuation of a trigger lever arrangement of the drive arrangement.

In accordance with a further embodiment, the first plunger and the second plunger can be of equal size.

The present application in particular includes a system which comprises a dispensing device in accordance with any one of the preceding embodiments, as well as at least one multi-component cartridge for reception in the dispensing device.

The method for attaching a cartridge end of a multi-component cartridge in a dispensing device comprises the following steps: insertion of the cartridge end of the multi-component cartridge into a reception element in an assembly position which is rotatably arranged in the housing, wherein the cartridge end is located at the inlet side of a first and second storage container filled with a filling mass and respectively sealed in a fluid-tight manner at the cartridge end by a respective piston; rotation of the cartridge element and the reception element rotationally fixedly connected with the cartridge end into a dispensing position.

In particular, the assembly position and/or the dispensing position can be determined by an abutment or a latch element, it is also possible to secure the assembly position and/or the dispensing position, in particular by means of the abutment and/or of the latch element.

The fixing can include a latching, with a clicking sound being able to be generated on latching which signals to the user that a latching has taken place.

By rotating in the opposite direction the cartridge end can be led back into the assembly position from the dispensing position. In the assembly position the cartridge end can be removed from the reception element.

The reception element can have a coding element. The storage containers can be correctly connected with the dispensing device by means of the coding element. The correct connection is essential for different mixing ratios for which the fact applies that the plungers can have different sizes.

The plungers are moved by a drive arrangement. The drive arrangement includes a trigger lever arrangement in accordance with one of the embodiments. By actuating the trigger lever arrangement a feeding mechanism connected with the trigger lever arrangement is actuated, so that a movement of the plunger in the direction of the dispensing end of the multi-component cartridge takes place. The feeding mechanism includes at least one rotatable finger element which interacts with a toothed track attached at the plunger arrangement. Analog to this it would also be plausible to provide a clamping element at this position. By means of the clamping element the plunger arrangement can be moved in accordance with an alternative non-illustrated embodiment via a friction closure.

By means of the movement of the plunger a piston movably supported in the corresponding storage container of the multi-component cartridge is displaced in the direction of the dispensing end of the multi-component cartridge in the dispensing position. Hereby the filling volume of the corresponding storage container is reduced and the filling mass is dispensed via the dispensing end of the multi-component cartridge. A mixer can be attached at the dispensing end of the multi-component cartridge. This mixer can include a static mixing element in order to mix the components of the filling mass of each storage container with one another.

Additional features and advantages are described herein, and will be apparent from the following Detailed Description and the figures.

DETAILED DESCRIPTION

Figure 1:
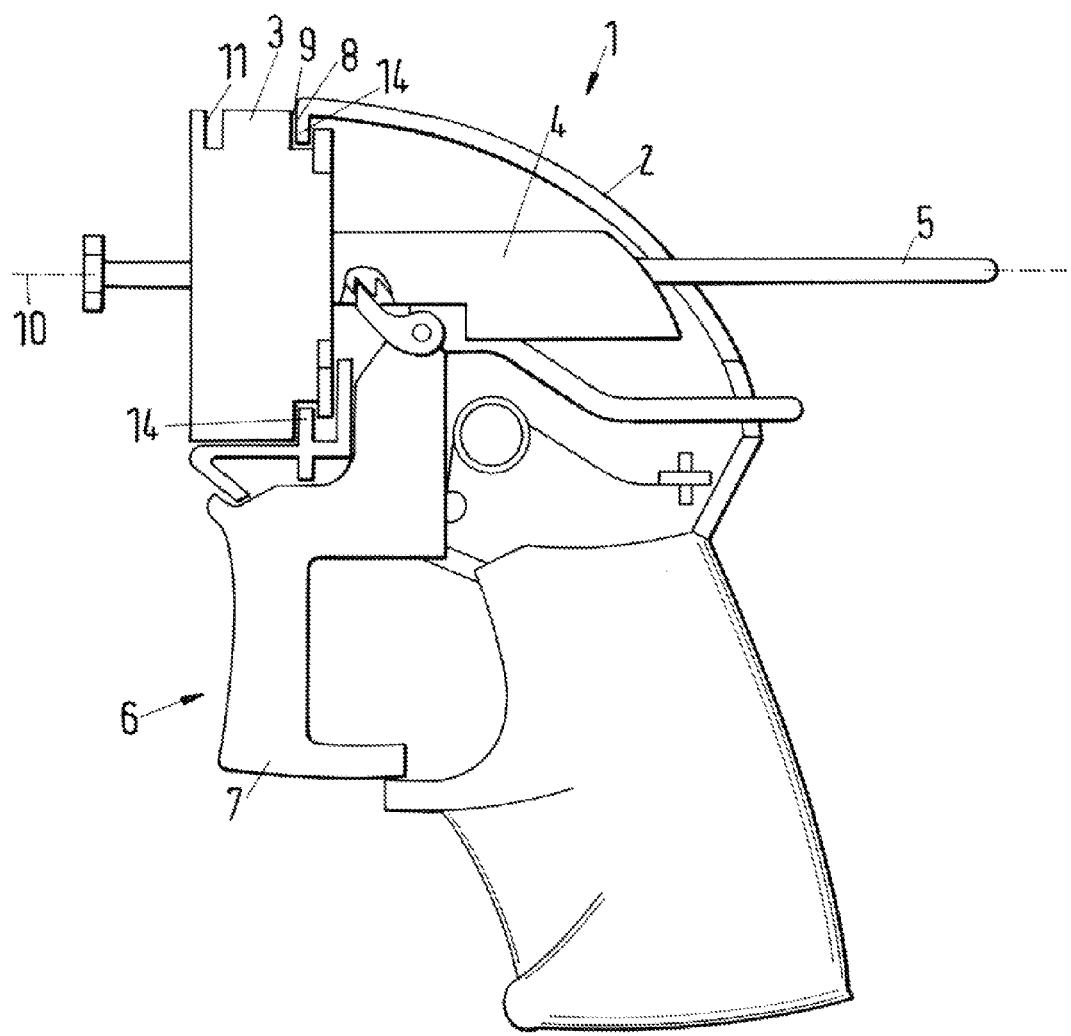
FIG. 1 a longitudinal section through a dispensing device in accordance with a first embodiment in which a part of the housing has been removed.

A longitudinal section through a dispensing device 1 in accordance with a first embodiment is illustrated in FIG. 1. A part of the housing 2 is removed in order to illustrate the arrangement of the individual components of the dispensing device as visible parts. A reception element 3 for receiving a cartridge end of the multi-component cartridge is arranged in the housing 2. Such a multi-component cartridge is shown, for example in FIG. 2. The cartridge end of the multi-component cartridge is located at the inlet side of the cartridge and includes a plurality of storage containers filled with a filling mass and each respectively sealed by a piston in a fluid-tight manner. Two storage containers are shown in the present arrangement.

The multi-component cartridge is not illustrated in FIG. 1 in order to not make the illustration too unclear. The reception element 3 includes openings through which a plunger arrangement 5 can be moved. A mount 4 for the plunger arrangement 5 is further present in the housing 2. The plunger arrangement 5 includes two plungers supported on a guide rail. The plungers are displaceable in a horizontal direction in FIG. 1. These press on the pistons of the multi-component cartridge and move these in the direction of the dispensing end of the multi-component cartridge. Hereby the filling mass present in the storage containers is dispensed.

The movement of the plungers takes place by means of a drive arrangement 6 serving for the movement of the plunger arrangement 5. A movement of the plunger arrangement 5 in a direction of a dispensing end of the multi-component cartridge can take place by actuating a trigger lever arrangement 7.

This direction of movement in the direction of a dispensing end is referred to as dispensing direction for dispensing the filling mass from the storage containers of the multi-component cartridge. The movement of the plunger arrangement 5 takes place along a longitudinal axis running through the plunger arrangement 5.

The reception element has an axis of rotation 10 which is substantially arranged in parallel to the dispensing direction. The cartridge end pushed into the reception element 3 is transferred from an assembly position into the dispensing position by a rotation about the axis of rotation 10. The reception element 3 is rotatably arranged in a guide element 8. The guide element 8 is arranged in the housing 2 and can, in particular be formed as a part of the housing and therefore be inseparably connected with the housing 2. In accordance with FIG. 1 the guide element 8 is a projection 14 which can be guided into a groove 9 of the reception element. The groove is formed as an at least partially surrounding groove 9. The projection 14 can be composed of several parts arranged at the circumference of the guide elements 8.

Figure 2:
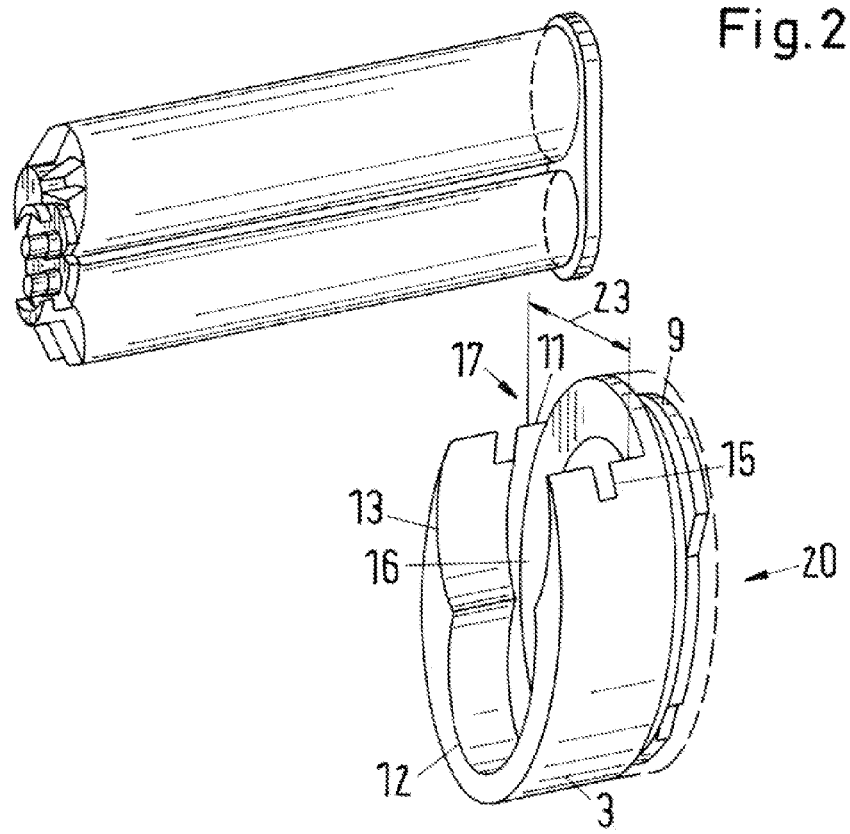
FIG. 2 a reception element in accordance with a first embodiment and a two-component cartridge which is intended for being receiving in the reception element.

FIG. 2 shows the reception element 3 in accordance with the first embodiments and a two-component cartridge which is intended to be received in the reception element 3. The reception element 3 is a substantially cylindrical body in the basic shape which is held in the housing 2 via the groove 9 which has been omitted in FIG. 3.

The cartridge end in most cases has a flange for connecting the two storage containers of the multi-component cartridge at the inlet side. This flange is introduced on assembly of the cartridge into a guide groove 11 arranged in the reception element 3 which serves for the receiving of the cartridge end. The guide groove 11 is part of a hollow space 16 present in the reception element which has substantially the shape of the cartridge end, in particular of the flange of the cartridge end. The hollow space 16 has a first front-side opening 12 and a second front-side opening 13 which in the assembled state receives the storage containers in a multi-component cartridge.

Furthermore, the hollow space has an opening 17 in the jacket of the reception element which enables an insertion into the cartridge end and an extraction out of the cartridge end. The opening 17 is precisely so large that the cartridge end can be inserted into the reception element such that the two storage containers can be inserted one after the other, this means that the first storage container is displaced via the second opening 13 intended for the second storage container in order to arrive in the position in which it is coaxially arranged with respect to the first opening 12 intended for the first storage container. This means that the cartridge end is inserted into the reception element such that the cartridge end is pushed over the second opening 13 in order to cover the first opening 12. On assembly of the cartridge end and the reception element, the storage containers are therefore displaced between the second opening 13 and the first opening 12 along a connection line lying in a plane normal to their longitudinal axes connecting precisely these longitudinal axes.

The opening 17 therefore has a maximum width dimension 23 which substantially corresponds to the width dimension of the flange. The depth of the hollow space corresponds at least to the longitudinal dimension of the flange. This arrangement has the advantage that the smallest possible part of the jacket surface of the reception element 3 is consumed for the jacket-side opening 17. This leads to a minimum weakening of the reception element 3 and therefore increases the stiffness and robustness of the reception element 3.

When the dispensing device is held in a vertical position and the reception element 3 is located in the assembly position 20, the opening 17 is preferably at the top. This means that the cartridge is installed from the top and so crossways to the dispensing direction in this preferred variant.

Figure 3:
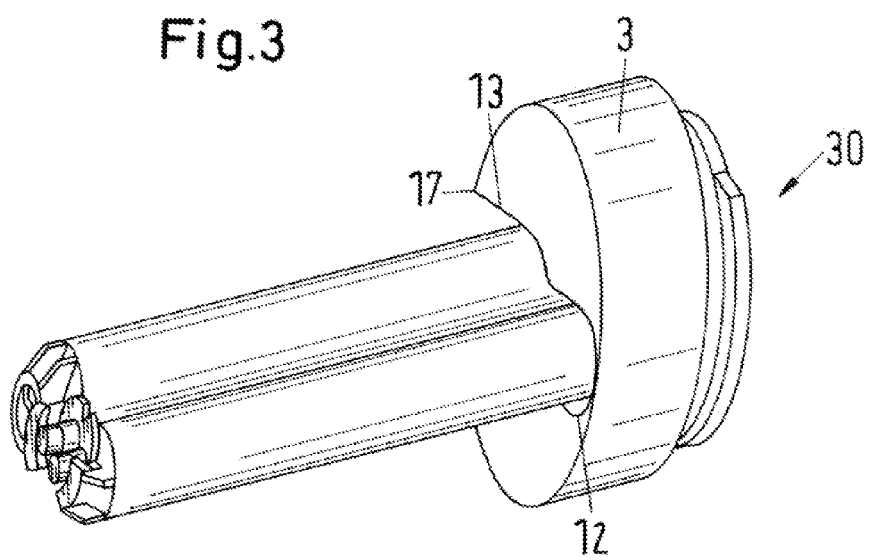
FIG. 3 the reception element in accordance with FIG. 2 with the two-component cartridge being received therein.

FIG. 3 shows the reception element in accordance with FIG. 2 with the therein received two-component cartridge. The angle of rotation from the assembly position 20 into the dispensing position 30 amounts to substantially 90°. In FIG. 3 it is clear that the jacket-side opening 17 is brought to lie in a lateral position by means of a rotation from the upper position, so that the cartridge takes up a substantially horizontal position. When the dispensing device is held in the vertical position the first and second openings 12, 13 lie substantially next to one another so that the longitudinal axis of the storage containers are arranged substantially in a horizontal plane.

Figure 4:
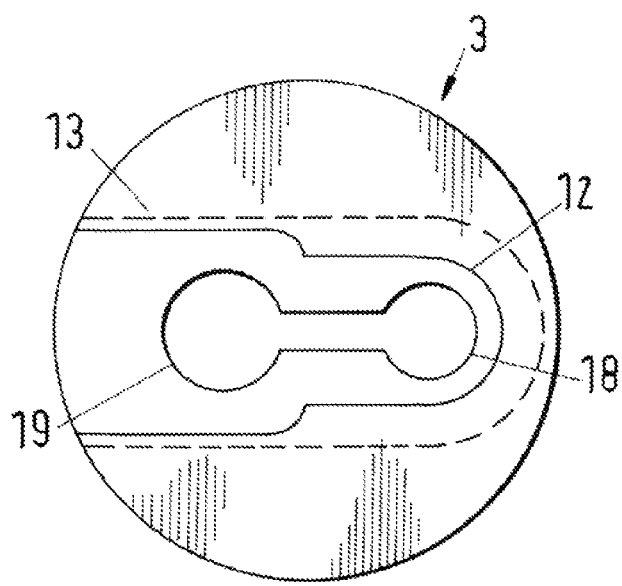
FIG. 4 a view of the reception element in accordance with FIG. 2 from the cartridge side.

FIG. 4 shows a view of the reception element in accordance with FIG. 2 from the cartridge side in the installed state. The first and second openings 12, 13 are shown in the position corresponding to the dispensing position. Furthermore, the recesses 18, 19 for the two plungers are shown in the illustration of FIG. 4. The recesses 18, 19 are substantially circular. The diameter of the recess 18 is smaller than the diameter of the recess 19. This arrangement is suitable for multi-component cartridges whose mixing ratios amount to at least 4:1. In particular, the mixing ratio can amount to 10:1 or lie above that. The filling volume can be at least 10 ml, preferably at least 25 ml, particularly preferably 50 ml. The filling volume can amount to at most 200 ml preferably to at most 75 ml.

Figure 5:
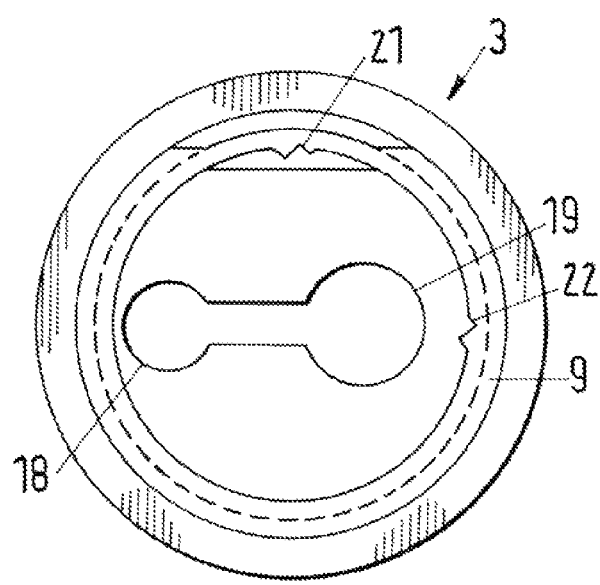
FIG. 5 a view of the reception element from the side which is received in the housing of the dispensing device.

FIG. 5 shows a view of the reception element from the side which is received in the housing of the dispensing device. The recesses 18 and 19 for the plunger are also shown like the groove 9 which groove serves for the reception of the guide element arranged in the housing. Furthermore, a latch element 21, as well as a latch element 22 are shown. The latch element 21 causes a fixing of the reception element in the dispensing position 30, the latch element 22 causes a latching of the reception element in the assembly position 20.

Figure 6:
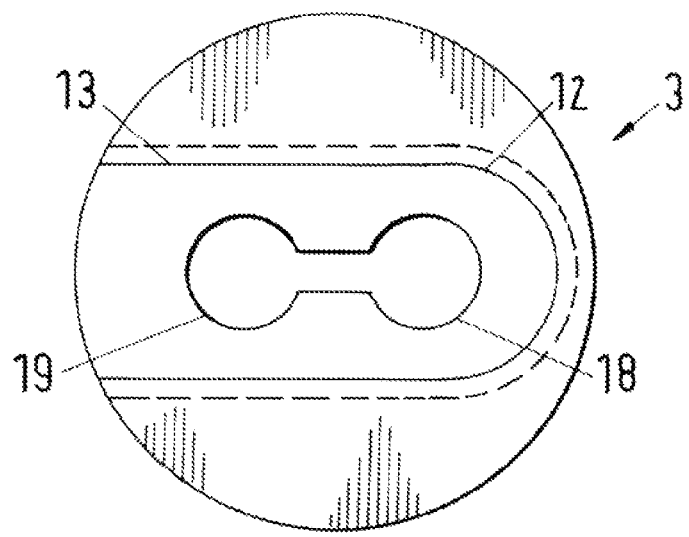
FIG. 6 a view of the reception element in accordance with a second embodiment from the cartridge side.
Figure 7:
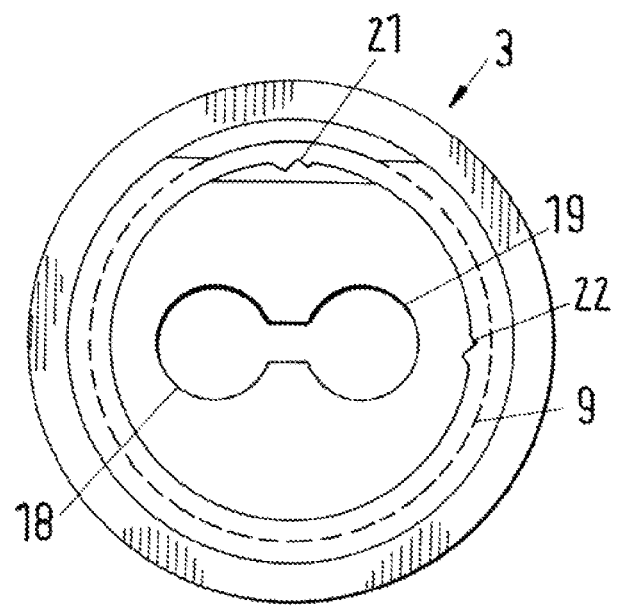
FIG. 7 a view of the reception element from the side which is received in the housing of the dispensing device.

FIG. 6 shows a view of the reception element in accordance with a second embodiment from the cartridge side in the installed state. The first and the second opening 12, 13 are shown in the position which corresponds to the dispensing position. Furthermore, the recesses 18, 19 for the two plungers are shown in the illustration of FIG. 4. The recesses 18, 19 are substantially circular. The diameter of the recess 18 is of equal size to the diameter of the recess 19. This arrangement is suitable for multi-component cartridges whose mixing ratios amount to 1:1 or do not substantially depart from this. In particular, the mixing ratio can amount to up to 2:1. The filling volume can be at least 10 ml, preferably at least 25 ml, particularly preferably 50 ml. The filling volume can be at most 200 ml, preferably at most 75 ml. FIG. 7 shows a view of the reception element from the side which is received in the housing of the dispensing device. With the exception of the recesses 18, 19 which are formed corresponding to FIG. 6, the same elements are used in FIG. 7 so that one can refer to the description with regard to FIG. 5.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dispensing device for a multi component cartridge including a housing in which a reception element for receiving a cartridge end of the multicomponent cartridge is arranged, wherein the cartridge end is located at the inlet side of a first and second storage container filled with a filling mass and respectively sealed in a fluid tight manner at the cartridge end by a respective piston, wherein a plunger arrangement and a drive arrangement for moving the plunger arrangement are arranged in the housing, wherein a movement of the plunger arrangement in a dispensing direction can be carried out by the drive arrangement for dispensing the filling mass from the storage containers of the multicomponent cartridge, wherein the reception element has an axis of rotation which is substantially arranged in parallel to the dispensing direction, wherein the cartridge end pushed into the reception element can be transferred from an assembly position into a dispensing position by a rotation about the axis of rotation, the assembly position being different from the dispensing position, wherein the assembly position allows the cartridge end to be installed into and removed from the reception element whereas the dispensing position allows dispensing of the filling mass by movement of the plunger arrangement, the reception element is rotatably arranged in a guide element, and the reception element or the guide element has an abutment in order to limit the rotation between the assembly position and the dispensing position.

2. A dispensing device in accordance with claim 1, wherein an angle of rotation from the assembly position into the dispensing position amounts to substantially 90°.

3. A dispensing device in accordance with claim 1, wherein the guide element is arranged in the housing in an installed state and is inseparably connected to the housing in the installed state.

4. A dispensing device in accordance with claim 1 wherein the reception element is rotatably supported in the guide element in the housing.

5. A dispensing device in accordance with claim 1, wherein the guide element is formed as a projection which can be received in a groove of the reception element.

6. A dispensing device in accordance with claim 1, wherein, on assembly of the cartridge end and the reception element, longitudinal axes of the first and second storage containers are displaceable along a connection line between a second opening for the second storage container and a first opening for the first storage container.

7. A dispensing device in accordance with claim 1, wherein the reception element has a guide groove for receiving the cartridge end.

8. A dispensing device in accordance with claim 1, wherein the reception element has at least one of an abutment and a latching element for securing the multicomponent cartridge in at least one of the dispensing position and the assembly position.

9. A dispensing device in accordance with claim 8, wherein a clicking sound can be emitted on latching, so that the latching is audible for the user.

10. A dispensing device in accordance with claim 8, wherein the cartridge end can be inserted into the reception element and can be removed again from the reception element.

11. A dispensing device in accordance with claim 1, wherein the reception element has a coding element for a correct positioning of the first and second storage containers of the multicomponent cartridge.

12. A dispensing device in accordance with claim 11, wherein the coding element includes a first opening and a second opening in which a respective storage container of the multicomponent cartridge can be received, with a diameter of the first opening being different from a diameter of the second opening.

13. A dispensing device in accordance with claim 1, wherein a movement of the plunger arrangement in the direction of a dispensing end of the multicomponent cartridge takes place by means of an actuation of a trigger lever arrangement of the drive arrangement.

14. A dispensing device in accordance with claim 1, wherein the reception element has a latching element for latching the reception element in at least one of the dispensing position and the assembly position.

* * * * *